United States Patent
Burgfels et al.

(10) Patent No.: US 6,951,638 B1
(45) Date of Patent: Oct. 4, 2005

(54) PROCESS FOR PRODUCING SYNTHETIC ZEOLITES WITH AN MFI STRUCTURE

(75) Inventors: Götz Burgfels, Bad Aibling (DE); Josef Schönlinner, Obing (DE); Friedrich Schmidt, Rosenheim (DE)

(73) Assignee: Sud-Chemie AG, Munich (DE)

( * ) Notice: Subject to any disclaimer, the term of this patent is extended or adjusted under 35 U.S.C. 154(b) by 82 days.

(21) Appl. No.: 10/111,651

(22) PCT Filed: Oct. 11, 2000

(86) PCT No.: PCT/EP00/10012
§ 371 (c)(1),
(2), (4) Date: Sep. 3, 2002

(87) PCT Pub. No.: WO01/30697
PCT Pub. Date: May 3, 2001

(30) Foreign Application Priority Data
Oct. 27, 1999 (DE) .......................... 199 51 781

(51) Int. Cl.$^7$ ............................................ C01B 39/40
(52) U.S. Cl. ........................ 423/709; 423/702; 423/716; 423/DIG. 22; 502/71; 502/77
(58) Field of Search ................................ 423/702, 709, 423/DIG. 22; 502/63, 647, 71, 73, 77, 64

(56) References Cited

U.S. PATENT DOCUMENTS

| | | | |
|---|---|---|---|
| 4,526,879 A | * 7/1985 | Dwyer et al. ................. | 502/71 |
| 5,102,644 A | * 4/1992 | Plank et al. ................. | 423/700 |
| 5,110,573 A | * 5/1992 | Johnson ...................... | 423/705 |
| 5,174,977 A | 12/1992 | Chang et al. | |
| 5,174,978 A | 12/1992 | Hellring et al. | |
| 5,174,981 A | 12/1992 | Hellring et al. | |
| 5,209,918 A | 5/1993 | Hellring et al. | |
| 5,240,892 A | * 8/1993 | Klocke ......................... | 502/77 |
| 5,268,162 A | * 12/1993 | Ishida et al. ................. | 423/704 |
| 5,624,658 A | 4/1997 | Fitoussi et al. | |
| 5,672,331 A | * 9/1997 | Verduijn ...................... | 423/702 |
| 5,741,904 A | 4/1998 | Hoelderich et al. | |
| 5,783,321 A | 7/1998 | Verduijn et al. | |
| 6,074,457 A | 6/2000 | Anthonis et al. | |

FOREIGN PATENT DOCUMENTS

| | | |
|---|---|---|
| DE | 4405876 | 10/1995 |
| EP | 021675 | 9/1983 |
| EP | 110 650 | 6/1984 |
| EP | 753 483 | 1/1997 |
| EP | 753 485 | 1/1997 |
| GB | 1115489 | 5/1968 |
| GB | 2058033 | 10/1980 |
| GB | 2160517 | 12/1985 |
| JP | 62017014 | 1/1987 |
| JP | 62017015 | 1/1987 |
| SU | 1610776 | 1/1996 |
| WO | WO 93/25476 | 12/1993 |

* cited by examiner

Primary Examiner—David Sample
(74) Attorney, Agent, or Firm—Scott R. Cox

(57) ABSTRACT

A process is described for producing synthetic zeolites with a MFI structure, a Si/Al atomic ratio from roughly 8 to 45 and very small primary crystallites, a Si source, an Al source and an organic template being reacted with one another under hydrothermal conditions, the Si/Al atomic ratio being roughly 9 to 50 and the ratio between the longest and shortest axis of the primary crystallites being roughly 1.0 to 1.5:1; the process is characterized in that the reaction is carried out in the presence of seed crystals with an average particle size from roughly 10 to 100 nm, preferably from 20 to 50 nm from an earlier batch without separation from the mother liquor.

The zeolites as claimed in the invention which are characterized by the combination of the following features:

(a) Si/Al atomic ratio 8 to 45:1
(b) Size of the primary crystallites roughly 0.01 to 0.05 microns;
(c) Ratio between longest and shortest axis of the primary crystallites: roughly 1.0 to 1.5:1;
(d) Ratio between the intensity of the x-ray diffraction line with the highest intensity ($D_{max}$=3.865+/−0.015) and the intensity of the x-ray diffraction lines of ZSM 11-zeolite ($D_{max}$=11.15 angstroms); mordenite ($D_{max}$=9.06 angstroms); α-cristobalite ($D_{max}$=3.345 angstroms); and analcim ($D_{max}$=4.83 angstroms) >500:1.

One development of the process as claimed in the invention is characterized in that the reaction product is converted by ion exchange into the H form, moldings produced with the addition of binders and optionally catalytically active base metal and/or precious metal components are added before or after the moldings are produced.

The synthetic zeolites can be used as catalysts, especially as catalysts for acid-catalyzed reactions, oxidation, reduction and adsorption.

18 Claims, No Drawings

PROCESS FOR PRODUCING SYNTHETIC ZEOLITES WITH AN MFI STRUCTURE

SPECIFICATION

The invention relates to a process for producing synthetic zeolites with MFI structure.

DE-A-109 608 660 described a process for producing ε-caprolactam from cyclohexanonoxime in the gaseous phase using MFI catalysts with symmetrically arranged OH groups on their surface. The crystallite size of the MFI catalysts is <5, preferably 0.05 to 0.5 microns. The catalysts are produced by hydrothermal synthesis using tetrapropyl ammonium bromide. There are no indications of the use of seed crystals.

EP-B-0 568 566 describes a process for producing essentially binder-free zeolites with a $SiO_2/Al_2O_3$ ratio of more than 80, at an elevated temperature a zeolite aggregate which is bound to silicon dioxide being aged in an aqueous ionic solution which contains hydroxyl ions. Spherical crystallites with a diameter of <3 microns are obtained. There are no indications of the use of seed crystals.

EP-B-0 609 270 discloses a process for producing zeolites of the MFI type with a uniform crystal size in which (i) a source of particulate silicon dioxide with an average diameter of 1 micron or less; (ii) seed crystals of the MFI zeolite with an average diameter of 100 nm or less in the form of a colloidal suspension; (iii) an organic structure-directing agent (template); and (iv) a fluorine source and an alkali metal source are reacted with formation of an aqueous synthetic mixture, the seed crystals being present in an amount from 0.05 to 1700 ppm by weight of the synthesis mixture and the synthesis mixture having a basicity, expressed as a molar ratio of $OH^-/SiO_2$, of less than 0.1, and the synthesis mixture being left to crystallize. The crystals produced preferably have an average diameter or an average length of 0.3 to 30 microns.

The seed crystals can be obtained for example by grinding larger crystals into smaller crystals in a ball mill. According to the examples the seed crystals are produced separately from silicic acid, TPAOH, NaOH and water. They do not contain aluminum oxide since silicalites are used as the seed crystals. The seed crystals are separated from the mother liquor, washed separately until the wash water has a pH less than 10, and used as a "colloidal seed crystal suspension" ready for use.

EP-B-0 643 671 describes a crystalline tectosilicate-ZSM-5-zeolite which consists essentially of acicular agglomerates. The average ratio of length to diameter of these agglomerates is at least 2.5, the average length of the agglomerates usually being on the order of 0.20 to 10 microns, preferably 0.4 to 5 microns, The zeolite can be produced by crystallizing the synthesis mixture which contains (i) a silicon dioxide source; (ii) a source for aluminum, gallium, boron, iron, zinc or copper; or (iii) a source for a monovalent cation; and (IV) an organic structure control agent (template). The process is characterized in that the synthesis mixture originally contains 0.05 to 2000 ppm seed crystals of a MFI zeolite with an average maximum dimension of not more than 100 nm.

EP-A-0 753 483 describes a process for producing a MFI zeolite, a synthesis mixture being formed which is free of the organic templates, with a molar composition which corresponds to that of the zeolites to be produced and which contains the zeolite seed crystals with a maximum dimension of at most 100 nm; the seed crystal-containing synthesis mixture is hydrothermally treated. It was found that the presence of colloidal seed crystals in the zeolite synthesis mixture makes an organic template unnecessary. The crystallite sizes of the MFI zeolites according to the examples are between 1.2 and 2.8 microns. The crystallites are coffin-shaped.

WO 97/25272 describes a process for producing a MFI zeolite with a nonspherical crystal morphology, (a) an aqueous-alkali synthesis mixture with a silicic acid source and an organic template being reacted with (b) an active synthesis mixture which represents either (i) an aged aqueous-alkali synthesis mixture with a silicic acid source and an organic template or (ii) an active mother liquor which is derived from an aqueous synthesis mixture which was used for at least one crystallization and from which the crystals formed were removed, whereupon the mixture of (a) and (b) is hydrothermally treated in order to initiate crystallization.

EP-A-0 753 485 discloses the use of zeolite seed crystals with a particle size of at most 100 nm in order to accelerate the zeolite crystallization during thermal treatment of a zeolite synthesis mixture. Thermal treatment lasts no longer than 24 hours. The synthesis mixture contains at most 0.1% by weight seed crystals. A zeolite of the ZSM type is produced. The seed crystals used are produced specially, i.e. they are not contained in the mother liquor from a preceding synthesis. Since the seed crystals have left the mother liquor in which they crystallized, they have lower reactivity.

EP-A-0-021 675 discloses a continuous process for producing a crystalline zeolite with a "constraint index" between 1 and 11 and a $SiO_2/Al_2O_3$ ratio of more than 12, a mixture of sources of an alkali metal oxide ($R_2O$), an aluminum oxide, a silicon oxide and water being reacted using controlled amounts of reactants. The reaction takes place using seed crystals from the zeolite which results as the product.

U.S. Pat. No. 5,174,977, 5,174,978, 5,174,981 and 5,209,918 disclose zeolites of the ZSM-5 type and processes for their production. The seed crystals are specially produced seed crystals which do not originate from the mother liquor from a preceding synthesis.

Compared to this prior art, the object of the invention was to produce synthetic, phase-pure zeolites rich in aluminum with a MFI structure and spherical nanocrystalline crystallites.

This object is achieved as claimed in the invention by a process for producing synthetic zeolites with a MFI structure, a Si/Al atomic ratio from roughly 8 to 45 and very small primary crystallites, a Si source, an Al source and an organic template being reacted with one another under hydrothermal conditions, the Si/Al atomic ratio being roughly 9 to 50 and the ratio between the longest and shortest axis of the primary crystallites being roughly 1.0 to 1.5:1; the process is characterized in that the reaction is carried out in the presence of seed crystals with an average particle size from roughly 10 to 100 nm, preferably from 20 to 50 nm from an earlier batch without separation from the mother liquor.

The process as claimed in the invention compared to the prior art has the advantage that the seed crystals used need not be subjected to additional treatment steps, i.e. the seed crystals do not leave the favorable pH range of >11 in any stage of the process. The especially high activity of the seed crystals is ensured by this measure.

To determine the particle size of the seed crystals the particles were separated by means of a centrifuge from the mother liquor and were washed repeatedly with acetone. The resulting product was dried and then examined with a scanning electron microscope. In doing so a particle size from 20 to 50 nm was established. The particles were essentially spherical.

Preferably precipitated silicic acid is used as the Si source, sodium aluminate as the Al source and tetrapropyl ammonium bromide as the organic template.

Hydrothermal conversion is preferably carried out at a temperature from roughly 100 to 180° C., a pH from roughly 11 to 13, and at a weight ratio between the Si and Al source from roughly 2.95 to 26.5.

In a further treatment stage the reaction product is preferably dried and calcined.

The subject matter of the invention is furthermore synthetic zeolites with a MFI structure which can be obtained using the process described above and which are characterized by the combination of the following features:
(a) Si/Al atomic ratio 8 to 45:1
(b) Size of the primary crystallites roughly 0.01 to 0.05 microns;
(c) Ratio between longest and shortest axis of the primary crystallites: roughly 1.0 to 1.5:1;
(d) Ratio between the intensity of the x-ray diffraction line with the highest intensity ($D_{max}$=3.865+/−0.015) and the intensity of the x-ray diffraction lines of ZSM 11-zeolite ($D_{max}$=11.15 angstroms); mordenite ($D_{max}$=9.06 angstroms); α-cristobalite ($D_{max}$=3.345 angstroms); and analcim ($D_{max}$=4.83 angstroms)>500:1.

One development of the process as claimed in the invention is characterized in that the reaction product is converted by ion exchange into the H form, moldings produced with the addition of binders and optionally catalytically active base metal and/or precious metal components are added before or after the moldings are produced.

The synthetic zeolites as claimed in the invention can be used as catalysts, especially the zeolites in H form (with or without coating with base metals and/or precious metals) as catalysts for acid-catalyzed reactions, oxidations, reductions and adsorptions.

These reactions comprise among others catalytic cracking (FCC additive) and hydrocracking (also "dewaxing" by careful hydrocracking);

Alkylations, for example of aromatics with olefins, alcohols, or halogen-containing paraffins;

Alkylation of aromatics;

Alkylation of isoparaffins with olefins;

Transalkylation (of aromatics);

Disproportionating (for example, toluene disproportionating, etc);

Isomerization and hydroisomerization (for example, of paraffins, olefins, aromatics, xylene-isomerization, dewaxing, etc.);

Dimerization and oligomerization;

Polymerizations;

Etherification and esterification;

Hydration and dehydration;

Adsorption;

Condensation;

Oxidation;

Acetalization;

Dealkylation and cyclization;

Alkylation and hydrodealkylation (ethyl benzene to benzene);

Exhaust gas cleaning;

Acid-catalyzed reactions are given for example in DE-A-4 405 876, a catalyst based on a particulate acid-activated phyllosilicate being used which has particles joined to one another by a binder.

In their use as catalysts, the products as claimed in the invention are generally in lump form, for example as extrudates, granulates, pellets, balls, honeycombs and other molded bodies.

To achieve a certain strength, generally an inorganic, organometallic or organic binder is added to the masses for producing the moldings. Preferably silicic acid or aluminum hydroxide sols are used as the organic binders. Furthermore, aluminates, titanates or phosphates are suited. Especially suited are alkaline earth compounds which form poorly soluble salts when reacted with acid, strontium and barium compounds yielding better binders compared to the corresponding calcium compounds.

Furthermore, suitable inorganic binders are compounds of the metals of groups IIIA (preferably $Y_2O_3$), IIIB (preferably $B_2O_3$, $Al_2O_3$ or $Al(H_2PO_4)_3$), IVA (preferably $TiO_2$ and $ZrO_2$), IVB (preferably oxides, carbides or nitrides of silicon, lanthanoids, preferably $LaO_2$ or $CeO_2$) of the actinoids (preferably $ThO_2$).

Inorganic binders can be also hydraulic binders, preferably cement or gypsum, or natural silicate binders such as mullite or talc.

The organometallic binder can be a compound of formula $Me(OR)_n$ or of formula $Me(O-CO-R)_n$, in which Me is a metal with a valency n and R is an organic residue, for example an alkyl, aryl, aralkyl, alkaryl or heterocyclic residue.

The organic binder can be a natural, semisynthetic or synthetic polymer or a precursor thereof, which does not lose its binding properties under processing and/or application conditions. Examples are alkene (co)polymerizates, polycondensates, polyaddition compounds, silicone rubber, silicone resin, rubber, bone glue, casein, galalith, alginates, starch, cellulose, guar, carboxymethylcellulose, polyvinyl alcohol, polyacrylic or polymethacrylic compounds as well as addition or condensation resins. In particular furan resins or phenolic resins can be used.

Examples of binders are given in DE-A-4 405 876.

Inorganic, organometallic and/or organic binders can be combined with one another as claimed in the invention in a suitable manner. Here it can be advantageous to use at least some of the binders in their colloidal form and/or in soluble form. Some binders can themselves be catalytically active.

The relative weight ratio between the selected zeolites with MFI structure on the one hand and the binder on the other varies from roughly 20 to 80% by weight. The zeolite with the MFI structure is preferably present in an amount of more than roughly 50% by weight, especially more than 60% by weight.

The invention is explained by the following examples.

EXAMPLE 1

Production of Zeolites in Na Form 1.662 g of demineralized water, 5.24 g sodium hydroxide and 709.5 g sodium aluminate were heated to 80° C. with vigorous stirring until a clear solution was obtained which was then cooled to below 60° C.

20 liters of a mother liquor from an earlier batch which (analytically) contained 3.43% by weight $SiO_2$, 2.16% by weight $Na_2O$ and 5.5% by weight tetrapropyl ammonium bromide (TPABr) were placed in a separate vessel. The mother liquor furthermore contained roughly 0.1% by weight seed crystals with an average particle size from 20 to 50 nm. The seed crystals had the following (analytic) composition $SiO_2$:91.77% by weight, $Al_2O_3$ 3.49% by weight, atomic ratio Si/Al=26.4.

The mother liquor was diluted with roughly 6 liters of demineralized water, whereupon 1980 g TPABr and 6260 g precipitated silicic acid (silica VN3LCC-Degussa) were added. The mixture was stirred for 30 to 60 minutes, whereupon 2380 g of the first solution were added.

The mixture was homogenized for roughly 30 to 60 minutes. The pH of the gel was 12.7.

The synthesis mixture was placed in a 40 liter autoclave which was provided with a stirring mechanism, and gradually heated to roughly 130° C., stirring having been done with a stirrer speed of roughly 73 rpm. The pressure rose during the reaction gradually from 2.5 to 3.5 bar due to the decomposition of the TPABr.

After 20 hours, a first sample amount of 127 g in the form of a white, medium-viscosity suspension with a pH of 11.13 was removed. The sample was easily filtered via filter paper on a suction filter and washed in batches with 5×200 ml deionized water. The filter cake was dried for one hour at 120° C. A wide peak was detected by x-ray at a layer lattice distance (D) of 3.8720 angstroms, i.e. the product was essentially still amorphous.

After 61 hours, 149 g of a second specimen in the form of a white, medium-viscosity suspension with a pH of 12.01 were removed. This specimen was processed like the first specimen and showed an x-ray diffraction spectrum with a very pronounced peak at 3.8720 angstroms. The degree of crystallinity (peak area/underlying area) was 96.8%.

After 68 hours, synthesis was terminated and a third specimen, which was processed in the same way as the first and the second specimen, showed a degree of crystallinity of 97.9%.

The remainder of the batch was filtered on larger suction filters, 23.0 kg of filter cake and 12.47 kg of mother liquor having been obtained. The mother liquor had the following analysis: Si=0.82% by weight, Al=5 ppm, Na=1.22% by weight, OH=1.16% by weight, Br=3.71% by weight, TPABr=8.2% by weight. The mother liquor contained roughly 0.1% by weight seed crystals with an average particle size of roughly 30–40 nm and had a pH of 12.25. The mother liquor was used for the following batches.

The filter cake was homogenized by intensive stirring for roughly 30 minutes in 120 liters of deionized water, then allowed to sediment and the supernatant was poured off. The residue was washed 8 times with 100 liters of water at a time until a pH from 7.3 to 7.4 was obtained and the last wash water had electrical conductivity of 130 $\mu S$. The entire washing process lasted roughly 5 hours, 20.7 filter cake having been obtained.

The filter cake was dried at 120° C. for 48 hours and granulated on screen granulator (Alexander device) to a particle size of <2.0 mm. The yield of dry granulate was 6.3 kg.

The granulates were calcined in a layer thickness of 10 mm at 540° C.

The yield of calcined product was 5.75 kg.

Characterization:

GV 1000° C.=6.5%; Si=43.6%; Al=3.31%; Na=1.71%; C=182 ppm; Fe=208 ppm; Ca=257 ppm.

The Si/Al ratio was 12.65, the BET surface (according DIN/66132) was 352 $m^2/g$ and the crystallinity was 96.96%.

The proportion of foreign phases which occur in conventional zeolite syntheses was determined by comparison of the intensities of the x-ray diffraction lines with the highest intensity, for mordenite ($D_{max}$=9.06 angstroms); analcim ($D_{max}$=4.83 angstroms); and α-cristobalite ($D_{max}$=3.345 angstroms). The ratio between the intensity of the x-ray diffraction line of the product as claimed in the invention with the highest intensity ($D_{max}$=3.8720 angstroms) and those of the three comparison peaks was >500:1. The product as claimed in the invention is therefore phase-pure.

From the product obtained, scanning electron microscope (REM) photographs were prepared, crystallites with an average particle size of roughly 30 nm having been found.

The crystallites were essentially spherical, the ratio between the long and short axis having been roughly 1.0 to 1:1.5.

COMPARISON EXAMPLE 1

The approach from example 1 was repeated with the difference that a mother liquor with 3.3% by weight seed crystals with a particle size of 0.1 to 1 micron was used. The number of seed crystals corresponded to those in the mother liquor as in Example 1.

The test was stopped after 100 hours, since the product which had been removed form the autoclave showed no crystallinity (roughly comparable to the specimen removed after 20 hours in example 1).

EXAMPLE 2

Producing a Zeolite in H Form

To produce a zeolite in H form, 3300 g of the calcined product which was obtained according to Example 1 was mixed in a 20 liter vessel with a stirring mechanism with 14.88 liters of deionized water. The suspension was heated to 80° C. as it was stirred, whereupon 1624 g 37% hydrochloric acid were added. Stirring continued for one hour at 80° C., whereupon the solid was allowed to sediment within 30 minutes. The supernatant solution was withdrawn, whereupon 14.88 liters of deionized water and 1624 g of 37% hydrochloric acid were added. The suspension was heated to 80° C. as it was stirred, and stirred for one hour at 80° C. Then the solid was allowed to sediment within 2 minutes. The supernatant was withdrawn, and the residue was repeatedly washed with deionized water until the conductivity of the wash water was less than 100 $\mu S$. The residue was then filtered on a suction filter.

The washed filter cake was dried for 16 hours at 120° C., 2.92 kg of the dry product having been obtained. The dry product was calcined at 540° C. for 10 hours. The yield of calcined product in H form was 2.85 kg.

The product had the following properties.

Ignition loss: 6.7% by weight; Si 45.44% by weight; Al=2.71% by weight; Na=48 ppm; Fe=80 ppm; C=160 ppm.

The Si/Al ratio was 16.1 compared to 12.65 of the product according to Example 1. The difference was due to the fact that some of the aluminum was dissolved out during acid treatment.

The degree of crystallinity was 95.2%. The location of the main peak ($D_{max}$=3.856 angstroms) had essentially not changed at all. The distribution of crystallite sizes and the axial ratio were essentially identical to those of the product from Example 1.

EXAMPLE 3

Production of a Binder-Containing Granulate from Zeolites in H Form from Example 2

2200 g of the powder from Example 2 were stirred for roughly 25 minutes with 3500 g of a 25% silicic acid sol (stirrer at 60 rpm) until a plastic mass was obtained. To adjust the rheology, 44 g of hydroxymethyl-hydroxypropylcellulose (Na salt) were added to this mass, whereupon the mass was kneaded again for 10 minutes at 60 rpm. The mass was extruded using an extruder (Haendle PZVM8b) with a mouthpiece diameter of roughly 1.5 mm. The extrudates were cut into pieces 3 mm long.

The pieces of extrudate were subjected to ion exchange with ammonium nitrate to remove the sodium content (from the cellulose derivative), 2.44 kg of the extrudate pieces having been carefully stirred with 4.89 liters of deionized water and 0.37 kg of ammonium nitrate at 20° C. over an interval of 1.5 hours.

After settling of the extrudate pieces, the supernatant solution was poured off. The extrudate pieces were washed several times. After the eighth washing, the conductivity of the wash water was less than 70 $\mu$S. The extrudate pieces were dried for 16 hours at 120° C., the yield having been 2.40 kg.

The dried product was calcined at 600° C. The yield of calcined product was 2.35 kg.

The calcined product had the following properties:
Binder content 30% by weight $SiO_2$, Na content: 50 ppm; remaining composition as according to Example 2:
Degree of crystallinity: 86.4%
Lateral compressive strength: 1.8 kp/3 mm, determined with a Schleuniger model 6D
Bulk weight: 550 g/liter;
Pore volume (determined according to Hg intrusion method with a porosimeter 4,000)=0.36 $cm^3$/g
Pore size distribution: >1750 nm=1.3%, 1750–80 nm=17.4%; 80 to 17 nm=45.6%; 14 to 7.5 nm=26.7%.
Average pore radius: 4 nm
Specific surface (BET) 328 $m^2$/g

EXAMPLE 4

Coating the Granulate from Example 3 with Platinum

In 35 ml of distilled water, 0.287 g hexachloroplatinic acid ($H_2PtCl_6$=10% by weight) were put into solution while stirring. 100 g of the granulates from Example 3 were poured into a test tube with this solution onto the top and intensively shaken, so that all granulates were uniformly wetted.

The impregnated granulates were dried for 16 hours at 120° C. and heated with a heat-up rate of 1° C./min in air to 450° C., whereupon this temperature was maintained for another 5 hours.

COMPARISON EXAMPLE 2

According to the method described by S. Ernst and J. Weitkamp (Chem.Ing.-Tech; 63; 748; 1991) zeolite synthesis was done without a template (TPABr). The Si/Al atomic ratio in the synthesis mixture was 35:1. The raw materials were the following chemicals: colloidal silica sol (Syton X30; Monsanto); distilled water; technical caustic soda Prills (Hoechst); sodium aluminate (Riedel de Haen).

After a reaction time of 112 hours at 160° C. a MFI zeolite contaminated with ZSM-11 (D=3.81 angstroms) and α-cristobalite ($D_{max}$=4.041 angstroms) was obtained (ratio of peak intensities 100:59.76 and 100:32.52). In the example as claimed in the invention the foreign phase proportions were below the detection limit of 100:0.2.

When examined using scanning electron microscopy, a primary crystallite size of 0.5 to 2 microns was ascertained. The primary crystallites had an average axial ratio of 2.5 to 1.

EXAMPLE 5

Producing Zeolites in Na Form 1664 g demineralized water, 226.8 g sodium hydroxide and 365 g sodium aluminate were heated to 80° C. while being vigorously stirred until a clear solution was obtained which was then cooled to below 60° C.

22 kg of a mother liquor from an earlier batch which (analytically) contained 3.43% by weight $SiO_2$, 2.16% by weight $Na_2O$ and 5.5% by weight tetrapropyl ammonium bromide (TPABr) were placed in a separate vessel. The mother liquor furthermore contained roughly 0.1% by weight seed crystals with an average particle size from 20 to 50 nm. The seed crystals had the following (analytic) composition: $SiO_2$: 91.77% by weight, $Al_2O_3$ 3.49% by weight, atomic ratio Si/Al=26.4.

The mother liquor was diluted with 4280 g of demineralized water, whereupon 1881 g TPABr and 6209 g precipitating silicic acid (silica FK320-Degussa) were added. The mixture was stirred for 30 to 60 minutes, whereupon 2247 g of the first solution were added.

The mixture was homogenized for roughly 30 to 60 minutes. The pH of the gel was 12.7.

The synthesis mixture was placed in a 40 liter autoclave which was provided with a stirring mechanism, and gradually heated to roughly 130° C., stirring having been done with a stirring speed of roughly 73 rpm. The pressure rose during the reaction gradually from 2.6 to 3.1 bar due to the decomposition of the TPABr.

After 63 hours, a first sample amount of 143 g in the form of a white, medium-viscosity suspension with a pH of 12.05 was removed. The sample was easily filtered via filter paper on a suction filter and washed in batches with 5×200 ml deionized water. The filter cake was dried for one hour at 120° C. X-ray examination of the specimen showed a pronounced peak at 3.87 angstroms. The degree of crystallinity (peak area/underlying area) was 97.9%.

After 80 hours, synthesis was terminated and a second specimen, which was processed in the same way as the first, showed likewise a degree of crystallinity of 97.9%.

Most of the batch was filtered on a suction filter, 16.7 kg of filter cake and 19.5 kg of mother liquor having been obtained. The mother liquor was not examined in detail.

The filter cake was homogenized by intensive stirring for roughly 30 minutes in 120 liters of deionized water, then allowed to sediment and the supernatant was poured off. The residue was washed 7 times with 100 liters of water at a time until a pH from 7.7 to 7.8 was obtained and the last wash water had electrical conductivity of 170 $\mu$S. The entire washing process lasted roughly 6 hours, 16.35 kg of filter cake having been obtained.

The filter cake was dried at 120° C. for 48 hours and granulated on screen granulator (Alexander device) to a particle size of <2.0 mm. The yield of dry granulates was 6.1 kg.

The granulates were calcined in a layer thickness of 10 mm at 540° C.

The yield of calcined product was 5.4 kg.

Characterization:
GV 1000° C.=5.9% by weight; Si=44.8% by weight; Al=1.86% by weight; Na=0/56% by weight; C=201 ppm The Si/Al ratio was 23.1, the BET surface (according DIN/66132) was 379 $m^2$/g and the crystallinity was 97.8%.

X-ray examination yielded no indication of foreign phases such as mordenite, analcim, or ZSM-11.

From the product obtained, scanning electron microscope (REM) photographs were prepared, crystallites with an average particle size of roughly 30 nm having been found. The crystallites were essentially spherical, the ratio between the long and short axis having been roughly 1.0 to 1:1.5.

EXAMPLE 6

Producing Zeolites in H Form

To produce a zeolite in H form, 2750 g of the zeolites produced according to Example 5 were mixed in a 20 liter vessel with a stirring mechanism with 12.4 kg of deionized water. The suspension was heated to 80° C. as it was stirred, whereupon 1356 g 37% nitric (62%) were added. After stirring for one hour at 80° C., the stirring device was turned off and the solid was allowed to sediment. The supernatant solution was withdrawn and the residue washed with several portions of deionized water until the conductivity of the wash water was 100 $\mu$S. The residue was then filtered on a suction filter.

The washed filter cake was dried for 16 hours at 120° C., 2.625 kg of the dry product having been obtained. The dried product was calcined at 540° C. for 10 hours. The yield of calcined product in H form was 2.580 kg.

The product was characterized as follows:
Ignition loss; 3.9% by weight; Si=44.18% by weight; Al=1.62% by weight; Na=94 ppm.

The Si/Al ratio was 26.2.

The crystallinity was 98.6%. The location of the main peak ($D_{max}$=3.856 angstroms) had essentially not changed at all. The distribution of crystallite sizes and the axial ratio were also essentially identical to those of the product from Example 1.

EXAMPLE 7

Production of a Binder-Containing Granulate from Zeolites in H Form from Example 6

2500 g of the zeolite powder from Example 6 were mixed with 734 g of a boehmite powder (aluminum oxide). 203 g of concentrated acetic acid and 2400 g of deionized water were added to this mixture. Upon further mixing a plastic mass formed. This plastic mass was mixed for another 30 minutes before it was extruded using a Haendle extruder of type PZVM8b with a mouthpiece diameter of roughly 1.5 mm. The extrudates were cut into pieces 3 mm long.

The pieces of extrudate were dried at 120° C. for 16 hours and then calcined for 5 hours at 600° C.

The resulting product had the following properties:
Binder content 20% by weight $Al_2O_3$; remaining composition as according to Example 6:
Crystallinity: 95.0%
Lateral compressive strength: 5.4 kp/3 mm, determined with a Schleuniger model 6 D
Bulk weight: 591 g/liter;
Pore volume (determined according to Hg intrusion method with a porosimeter 4,000)=0.36 $cm^3$/g
Pore size distribution: >1750 nm=0.3%, 1750–80 nm=1.4%; 80–17 nm=14.8%; 14–7.5 nm=83.3%.
Average pore radius: 6 nm
Specific surface (BET)=330 $m^2$/g

APPLICATION EXAMPLE 1

Use of Platinum-Free Catalyst According to Example 3 for Isomerization of M-Xylene and Hydrodealkylation of Ethyl Benzene (EB) to Benzene A special steel reactor 610 mm long with an inside diameter of 19 mm and electrical jacket heating was filled with 15 ml of the catalyst from Example 3 (diluted with 15 ml inert glass beads).

Activation is done at 300° C. for 12 hours under pure hydrogen (>99.95%). A defined hydrocarbon mixture of the composition described below is routed over the catalyst bed according to the operating conditions described below (test conditions) together with pure hydrogen (>99.95%). The composition of the product flow is determined by gas chromatography. The conversion of ethyl benzene (EB), xylene loss and concentration of p-xylene compared to the thermodynamic equilibrium value (p-xylene approach to equilibrium, PXATE) are computed:

| Composition of the hydrocarbon mixture (HC): | |
| --- | --- |
| Ethyl benzene (EB: | 15% by weight |
| m-Xylene: | 85% by weight |
| Test conditions: | |
| Temperature: | 400° C. |
| Pressure: | 28 barg |
| Space velocity LHSV: | 5.0 l/l/h |
| $H_2$/HC: | 2.0 mole/mole |
| Running time: | 11 hours |
| Catalyst performance: | |
| EB conversion: | 85.0% by weight |
| Xylene loss: | 28.1% by weight |
| PXATE: | 97.7% by weight |

Computation:
EB conversion %=(EB in−EB out)×100/EB in
Xylene los %=(Total xylenes in−total xylenes out)×100/total xylenes in
PXATE=(p-xylene isomer in the product normalized×100/ p-xylene isomer equilibrium)

APPLICATION EXAMPLE 2

Use of the Platinum-Containing Catalyst According to Example 4 for Xylene-Isomerization of M-Xylene and Hydrodealkylation of Ethyl Benzene (EB) to Benzene A special steel reactor 610 mm long with an inside diameter of 19 mm and electrical jacket heating was filled with 15 ml of the catalyst from Example 4 (diluted with 15 ml inert glass beads).

Activation is done at 300° C. for 12 hours under pure hydrogen (>99.95%).

A defined hydrocarbon mixture of the composition described below is routed over the catalyst bed according to the operating conditions described below (test conditions) together with pure hydrogen (>99.95%). The composition of the product flow is determined by gas chromatography. The conversion of ethyl benzene (EB), xylene loss and concentration of p-xylene compared to the thermodynamic equilibrium value (p-xylene approach to equilibrium, PXATE) are computed.

| Composition of the hydrocarbon mixture (HC): | |
| --- | --- |
| Ethyl benzene (EB): | 15% by weight |
| m-Xylene: | 85% by weight |
| Test conditions: | |
| Temperature: | 400° C. |
| Pressure: | 28 barg |

-continued

| | |
|---|---|
| Space velocity LHSV: | 5.0 l/l/h |
| $H_2$/HC: | 2.0 mole/mole |
| Running time: | 15 hours |
| Catalyst performance: | |
| EB conversion: | 96.0% by weight |
| Xylene loss: | 14.5% by weight |
| PXATE: | 89.1% by weight |

APPLICATION EXAMPLE 3

Use of Platinum-Containing Catalyst According to Example 4 for Isomerization of M-Xylene and Hydrodealkylation of Ethyl Benzene (EB) to Benzene A special steel reactor 610 mm long with an inside diameter of 19 mm and electrical jacket heating was filled with 15 ml of the catalyst from Example 4 (diluted with 15 ml inert glass beads).

Activation is done at 300° C. for 12 hours under pure hydrogen (>99.95%).

A defined hydrocarbon mixture of the composition described below is routed over the catalyst bed according to the operating conditions described below (test conditions) together with pure hydrogen (>99.95%). The composition of the product flow is determined by gas chromatography. The conversion of ethyl benzene (EB), xylene loss and concentration of p-xylene compared to the thermodynamic equilibrium value (p-xylene approach to equilibrium, PXATE) are computed

| Composition of the hydrocarbon mixture (HC): | |
|---|---|
| Ethyl benzene (EB): | 20% by weight |
| m-Xylene: | 80% by weight |

The test conditions and catalyst performance are summarized in Table 1.

TABLE I

| Temp. (° C.) | Pressure (barg) | LHSV (l/l/h) | $H_2$/HC mole/mole |
|---|---|---|---|
| 360 | 8.0 | 3.0 | 3.0 |
| 390 | 8.0 | 5.0 | 3.0 |
| 360 | 8.0 | 10.0 | 3.0 |
| 380 | 8.0 | 10.0 | 3.0 |

| Running time (hours) | EB conversion (% by weight) | Xylene loss (% by weight) | PXATE (%) |
|---|---|---|---|
| 360 | 86.1 | 9.0 | 101.6 |
| 49 | 95.3 | 8.8 | 101.6 |
| 293 | 57.9 | 4.4 | 101.8 |
| 188 | 74.5 | 6.4 | 101.8 |

APPLICATION EXAMPLE 4

Use of Platinum-Free Catalyst According to Example 3 for Isomerization of Xylenes A special steel reactor 290 mm long with an inside diameter of 37 mm and electrical jacket heating was filled with 250 ml of the catalyst from Example 3.

A defined hydrocarbon mixture of the composition described below is routed over the catalyst bed according to the operating conditions described below (test conditions). The composition of the product flow is determined by gas chromatography.

| Test conditions: | |
|---|---|
| Temperature: | 260° C., 280° C., 300° C. |
| Pressure: | 35 barg |
| Space velocity WHSV: | 10 l/l/h |

The composition of the loaded hydrocarbon mixture (HC) and the product distribution are summarized in Table II.

TABLE II

| | HC load | Product distribution (% by wt.) | | |
|---|---|---|---|---|
| HC name | (% by wt.) | 260° C. | 280° C. | 300° C. |
| Nonaromatics | 0.3 | 0.3 | 0.3 | 0.4 |
| Benzene | 0.1 | 0.1 | 0.1 | 0.1 |
| Toluene | 0.4 | 0.6 | 1.1 | 1.6 |
| EB | 0.3 | 0.3 | 0.3 | 0.3 |
| p-Xylene | 11.4 | 21.5 | 22.7 | 22.6 |
| m-Xylene | 54.3 | 50.5 | 50.7 | 50.2 |
| o-Xylene | 31.3 | 24.6 | 22.4 | 21.8 |
| $C_9^+$ aromatics | 1.9 | 2.1 | 2.4 | 3.0 |

EB: Ethyl benzene

APPLICATION EXAMPLE 5

Use of the Catalyst According to Example 7 for Disproportionating of Toluene A special steel reactor 610 mm long with an inside diameter of 19 mm and electrical jacket heating was filled with 15 ml of the catalyst from Example 7 (diluted with 15 ml inert glass beads).

A defined hydrocarbon mixture of the composition described below is routed over the catalyst bed according to the operating conditions described below (test conditions) together with pure hydrogen (>99.95%). The composition of the product flow is determined by gas chromatography.

| Test conditions: | |
|---|---|
| Temperature: | 400° C., 440° C., 480° C. |
| Pressure: | 15 barg |
| Space velocity LHSV: | 0.5 l/l/h |
| $H_2$/HC: | 3.0 mole/mole |

The composition of the loaded hydrocarbon mixture (HC) and the product distribution are summarized in Table III.

TABLE III

| | HC load | Product distribution (% by wt.) | | |
|---|---|---|---|---|
| HC name | (% by wt.) | 400° C. | 440° C. | 480° C. |
| Nonaromatics | 0.0 | 0.1 | 0.1 | 0.0 |
| Benzene | 0.0 | 8.2 | 15.5 | 31.8 |
| Toluene | 99.5 | 80.1 | 60.3 | 41.2 |

TABLE III-continued

| | HC load | Product distribution (% by wt.) | | |
|---|---|---|---|---|
| HC name | (% by wt.) | 400° C. | 440° C. | 480° C. |
| EB | 0.1 | 0.1 | 0.5 | 0.0 |
| p-Xylene | 0.1 | 2.6 | 5.0 | 5.4 |
| m-Xylene | 0.2 | 5.6 | 11.0 | 12.0 |
| o-Xylene | 0.1 | 2.4 | 5.0 | 5.3 |
| Σ $C_8$ | 0.5 | 10.7 | 21.5 | 22.7 |
| $C_9$ aromatics | 0.0 | 0.9 | 2.5 | 3.9 |
| $C_{10}^+$ aromatics | 0.0 | 0.0 | 0.1 | 0.4 |

EB: Ethyl benzene

APPLICATION EXAMPLE 6

Use of the Catalyst According to Example 7 for Transalkylation of Substituted Aromatics A special steel reactor 610 mm long with an inside diameter of 19 mm and electrical jacket heating was filled with 15 ml of the catalyst from Example 7 (diluted with 15 ml inert glass beads).

A defined hydrocarbon mixture of the composition described below is routed over the catalyst bed according to the operating conditions described below (test conditions) together with pure hydrogen (>99.95%). The composition of the product flow is determined by gas chromatography.

| Test conditions: | |
|---|---|
| Temperature: | 440° C., 480° C. |
| Pressure: | 15 barg |
| Space velocity LHSV: | 0.5 l/l/h |
| $H_2$/HC: | 3.0 mole/mole |

The composition of the loaded hydrocarbon mixture (HC) and the product distribution are summarized in Table IV.

TABLE IV

| | HC load | Product distribution (% by wt.) | |
|---|---|---|---|
| HC name | (% by wt.) | 440° C. | 480° C. |
| Nonaromatics | 0.3 | 0.8 | 0.1 |
| Benzene | 0.0 | 14.2 | 15.9 |
| Toluene | 0.0 | 38.3 | 41.2 |
| EB | 0.0 | 1.5 | 1.5 |
| p-Xylene | 0.0 | 6.6 | 6.6 |
| m-Xylene | 0.1 | 14.5 | 14.6 |
| o-Xylene | 0.4 | 6.5 | 6.7 |
| Σ $C_8$ | 0.5 | 29.1 | 29.4 |
| $C_9$ aromatics | 93.8 | 15.2 | 11.2 |
| $C_{10}^+$ aromatics | 5.4 | 2.4 | 2.2 |

APPLICATION EXAMPLE 7

Use of the Catalyst According to Example 7 for Conversion of Methanol into Higher Hydrocarbons A mixture of methanol and water is converted in a 2-reactor system consisting of a dimethyl ether (DME) prereactor R1 and a DME conversion reactor R2 into a mixture of (water and) hydrocarbons consisting of olefins, paraffins and aromatics. The conversion of methanol into DME and water takes place in a DME prereactor R1 by means of an acid catalyst, generally γ-$Al_2O_3$. Conversion of DME into higher hydrocarbons takes place in the DME conversion reactor R2 over the catalyst described in example 7.

The special steel reactor R1 which is 627 mm long with an inside diameter of 33.5 mm and electrical jacket heating is filled with 100 ml of commercial γ-$Al_2O_3$ (Sued-Chemie, 4.5×4.5 mm). The special steel reactor R2 which is 618 mm long with an inside diameter of 33.5 mm and electrical jacket heating is filled with 50 ml of the catalyst from example 7.

A defined hydrocarbon mixture of the composition described below is routed over the catalyst bed according to the operating conditions described below (test conditions) together with pure hydrogen (>99.996%). The composition of the product flow is determined by gas chromatography. The product distribution is summarized in Table V.

| Composition of the hydrocarbon/water mixture (HC): | |
|---|---|
| Methanol: | 80% by weight |
| Water: | 20% by weight |
| Test conditions: | |
| Temperature R1: | 320° C. |
| Temperature R2: | 300° C., 360° C. |
| Pressure: | 20 barg |
| Space velocity WHSV: | 20 g/g/h |
| $N_2$/HC: | 9.0 mole/mole |
| Methanol conversion: | >98% |

TABLE V

| | Product distribution (% by weight) | |
|---|---|---|
| HC name | 300° C. | 360° C. |
| $C_1$–$C_4$ | 36 | 50 |
| $C_5$–$C_8$ (PON) | 33 | 22 |
| Aromatics and $C_9^+$ | 31 | 28 |
| $C_5^+$ | 64 | 50 |

PON: Paraffins, olefins, naphthenes

APPLICATION EXAMPLE 8

Use of the Catalyst According to Example 7 for Oligomerization of Olefins

A special steel reactor 500 mm long with an inside diameter of 23 mm and electrical jacket heating is filled with 19 ml of the catalyst from Example 7 (diluted with 19 ml inert glass beads).

A defined hydrocarbon mixture of the composition described below is routed over the catalyst bed according to the operating conditions described below (test conditions) together with pure hydrogen (>99.95%). The composition of the product flow is determined by gas chromatography.

| Test conditions: | |
|---|---|
| Temperature: | 230° C. |
| Pressure: | 75 barg |
| Space velocity WHSV: | 1.0 g/g/h |

-continued

Test conditions:

| | |
|---|---|
| Running time: | 71 hours and 168 hours |
| Conversion $\Sigma_{butene}$: | >99% by mole |

The composition of the loaded hydrocarbon mixture (HC) and the product distribution of the liquid phase are summarized in Table VI.

TABLE VI

| | HC load | Product distribution liquid phase (% by wt.) | |
|---|---|---|---|
| HC name | (% by wt.) | 71 hrs | 168 hrs |
| $C_1$–$C_3$ | 0.4 | <$C_8$   6 | 6 |
| i-Butane | 32.0 | $C_8$   12 | 23 |
| n-Butane | 9.0 | >$C_8$–$C_{12}$   37 | 40 |
| 1-Butene | 14.0 | >$C_{12}$–$C_{16}$   26 | 22 |
| cis/trans-Butene | 29.0 | >$C_{16}$–$C_{20}$   12 | 7 |
| i-Butene | 15.0 | >$C_{20}$   7 | 2 |
| Other | 0.6 | | |

What is claimed is:

1. A process for producing synthetic zeolites with a MFI structure, a Si/Al atomic ratio of from about 8 to about 45:1 and small primary crystallites comprising reacting a Si source, an Al source and an organic template under hydrothermal conditions to produce a reaction product;

wherein the process is carried out in the presence of seed crystals of the zeolite with an average particle size from about 10 to 100 μm, without separation of the seed crystals from a mother liquor produced from an earlier synthetic zeolite production process.

2. The process of claim 1 wherein the hydrothermal reaction is accomplished at a temperature from about 100 to about 180° C.

3. The process of claim 1 wherein the concentration of the seed crystals in the reaction is from about 0.1 to about 0.2 percent by weight.

4. The process of claim 1 further comprising drying and calcining the reaction product.

5. The process of claim 1 further comprising converting the reaction product by ion exchange into its H-form.

6. The process of claim 1 further comprising producing moldings by the addition of a binder to the reaction product.

7. The process of claim 6 wherein the binder is selected from silicic acid and aluminum hydroxide.

8. The process of claim 6 wherein the binder is selected from compounds of metals selected from Group III.A, III.B, IV.A, IV.B and the actinium group of the periodic table.

9. The process of claim 6 wherein the binder is an inorganic binder selected from the group consisting of cement, gypsum and natural silicate binders.

10. The process of claim 6 wherein the binder comprises an organometallic binder with a formula $Me(OR)_N$ or $Me(O$—$CO$-$R)_N$, wherein Me is a metal with a valency of $N$ and R is an organic compound selected from alkyl, aryl, alkaryl and heterocyclic compounds.

11. The process of claim 6 wherein the weight ratio of the zeolite with the MFI structure to the binder is from about 1:4 to about 4:1.

12. The process of claim 6 wherein the weight ratio of the zeolite with the MFI structure to the binder is at least about 1:1.

13. The process of claim 1 further comprising producing moldings by the addition of catalytically active metals to the reaction product.

14. The process of claim 1 further comprising producing moldings by the addition of binders and precious metal components to the reaction product.

15. The process of claim 1 wherein the Si source comprises silicic acid, the Al source comprises sodium aluminate and the organic template comprising tetrapropyl ammonium bromide.

16. The process of claim 1 wherein the reaction is carried out at a pH between about 11 and 13.

17. The process of claim 1 wherein the weight ratio of the Si source to the Al source is from about 2.95 to 26.5:1.

18. The process of claim 1 wherein the atomic ratio of the Si:Al in the reaction is from about 9 to about 50:1.

* * * * *